(12) United States Patent
Page et al.

(10) Patent No.: US 6,869,395 B2
(45) Date of Patent: Mar. 22, 2005

(54) ENDOSCOPIC ACCESSORY ATTACHMENT MECHANISM

(75) Inventors: Edward C. Page, Baldwinville, MA (US); Theresa Methot, Westford, MA (US); Charles Patterson, Harmony, ME (US); Richard A. Clark, Holliston, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/275,226

(22) PCT Filed: May 14, 2001

(86) PCT No.: PCT/US01/40728
§ 371 (c)(1),
(2), (4) Date: Feb. 11, 2003

(87) PCT Pub. No.: WO01/87144
PCT Pub. Date: Nov. 22, 2001

(65) Prior Publication Data
US 2003/0171651 A1 Sep. 11, 2003

Related U.S. Application Data

(60) Provisional application No. 60/204,155, filed on May 15, 2000.

(51) Int. Cl.$^7$ ................................................. A61B 1/00
(52) U.S. Cl. ...................... 600/127; 600/129; 600/104
(58) Field of Search ................................. 600/104–107, 600/127–129

(56) References Cited

U.S. PATENT DOCUMENTS

| | | |
|---|---|---|
| 4,735,194 A | 4/1988 | Stiegmann |
| 4,825,259 A | 4/1989 | Berry, Jr. |
| 5,002,042 A | 3/1991 | Okada |
| 5,193,525 A | 3/1993 | Silverstein et al. |
| 5,259,366 A | 11/1993 | Reydel et al. |
| 5,269,789 A | 12/1993 | Chin et al. |
| 5,297,536 A | 3/1994 | Wilk |
| 5,320,630 A | 6/1994 | Ahmed |
| 5,398,844 A | 3/1995 | Zaslavsky et al. |
| 5,423,834 A | 6/1995 | Ahmed |
| 5,462,559 A | 10/1995 | Ahmed |
| 5,507,797 A | 4/1996 | Suzuki et al. |
| 5,624,453 A | 4/1997 | Ahmed |
| 5,681,328 A | 10/1997 | Lamport et al. |
| 5,697,940 A | 12/1997 | Chu et al. |
| 5,735,793 A | 4/1998 | Takahashi et al. |
| 5,782,776 A | 7/1998 | Hani |
| 5,788,715 A | 8/1998 | Watson, Jr. et al. |
| 5,853,416 A | 12/1998 | Tolkoff |

(List continued on next page.)

OTHER PUBLICATIONS

"RapidFire™ Multiple Band Ligator—Information for Use", Bard Interventional Products Division, C. R. Bard, Inc., No. AE1904601/01, Issued 06/96.

*Primary Examiner*—Beverly M. Flanagan
(74) *Attorney, Agent, or Firm*—Kirkpatrick & Lockhart Nicholson Graham LLP

(57) ABSTRACT

The present invention provides a mechanism for attaching accessory devices to the distal end of an endoscope or catheter. The engagement mechanism comprises a bracing member (392) that engages a surface of the endoscope (20) and a ramp surface (360), which applies a gripping force to an opposing surface of the endoscope, preferably through a wedge member (372). The bracing member (392) may comprise an elongate element that extends partially into the working channel of the endoscope or may comprise an element that engages a portion of the total circumference of the outside surface of the endoscope. The ramp surface (360) is inclined at an acute angle from the longitudinal axis of the endoscope and preferably engages with a slidable wedge in a cooperative arrangement that serves to reduce the distance between the wedge (372) and the bracing member (392) as the wedge slides on the ramp to engage a portion of the endoscope therebetween.

20 Claims, 16 Drawing Sheets

U.S. PATENT DOCUMENTS

| | | |
|---|---|---|
| 6,007,551 A | 12/1999 | Peifer et al. |
| 6,059,719 A | 5/2000 | Yamamoto et al. |
| 6,059,798 A | 5/2000 | Tolkoff |
| 6,071,233 A | 6/2000 | Ishikawa et al. |
| 6,099,535 A | 8/2000 | Lamport et al. |
| 6,136,009 A | 10/2000 | Mears |
| 6,241,140 B1 * | 6/2001 | Adams et al. ............ 227/180.1 |
| 6,280,452 B1 | 8/2001 | Mears |
| 6,436,108 B1 | 8/2002 | Mears |
| 6,689,130 B2 * | 2/2004 | Arai et al. .................... 606/46 |
| 2002/0177847 A1 * | 11/2002 | Long ........................... 606/46 |
| 2003/0167062 A1 * | 9/2003 | Gambale et al. ............ 606/138 |
| 2003/0176880 A1 * | 9/2003 | Long et al. ................. 606/167 |

\* cited by examiner

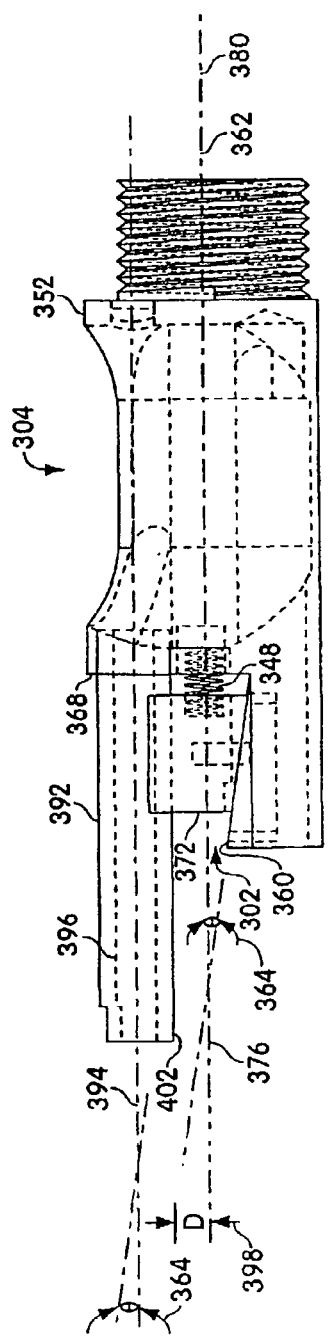
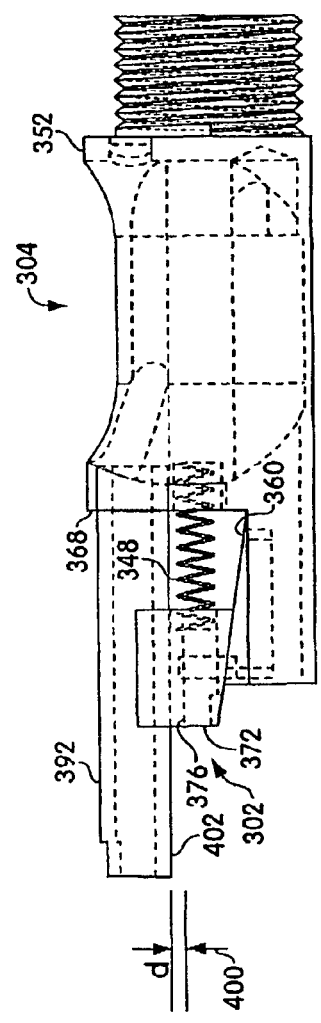
Fig. 11
Fig. 12

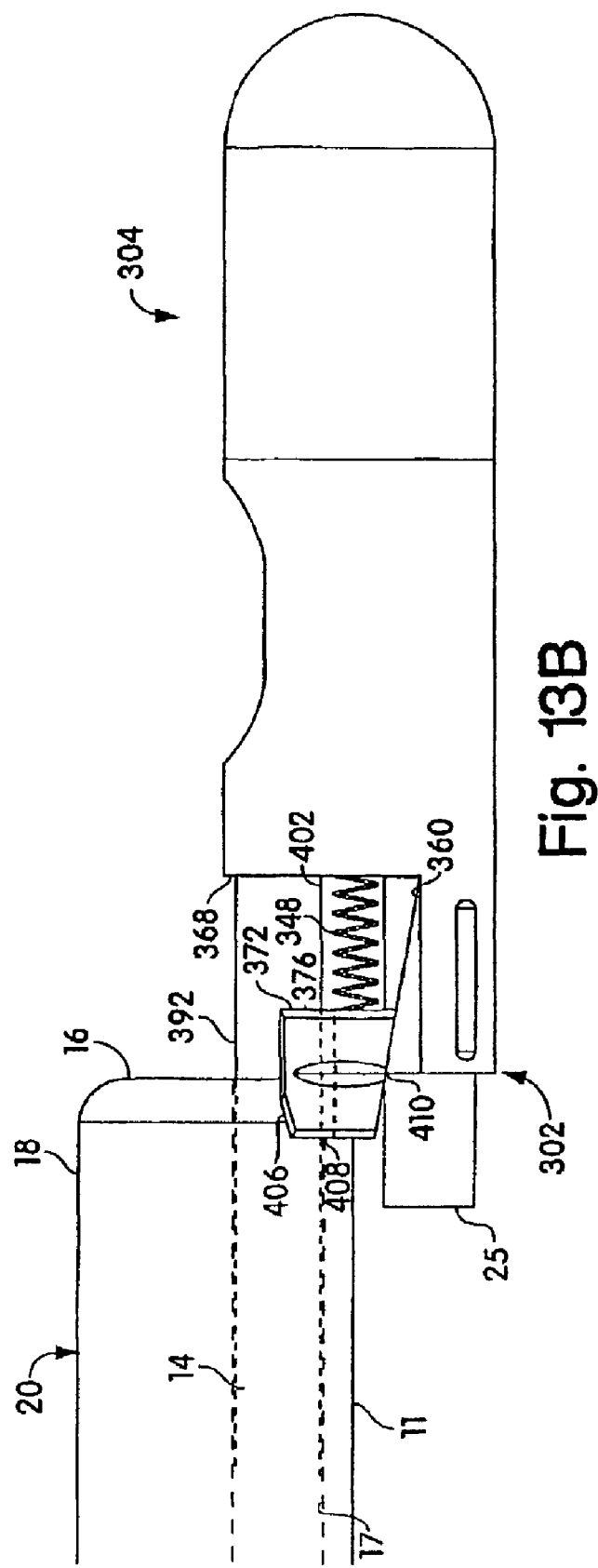

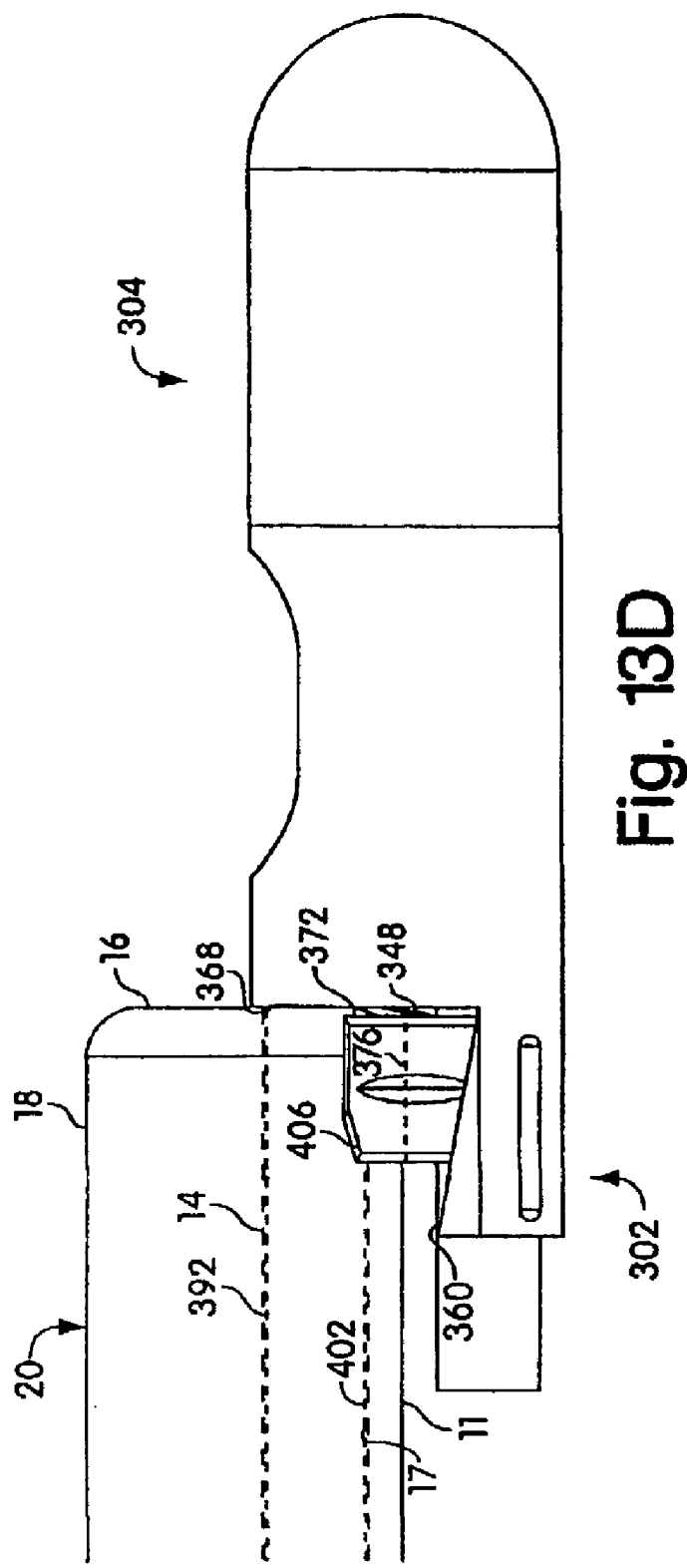

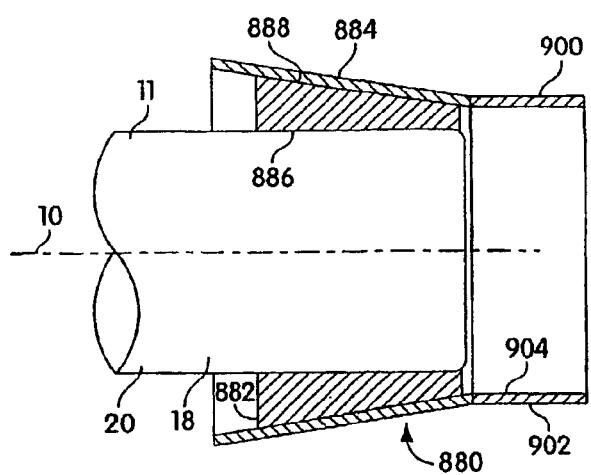 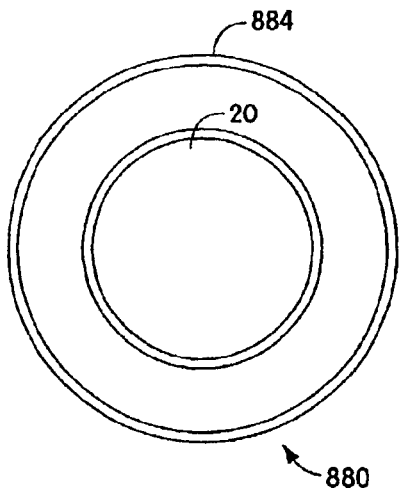
Fig. 20A  Fig. 20B
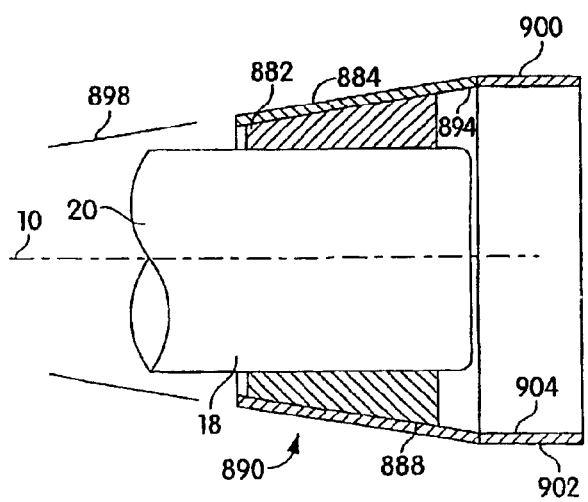 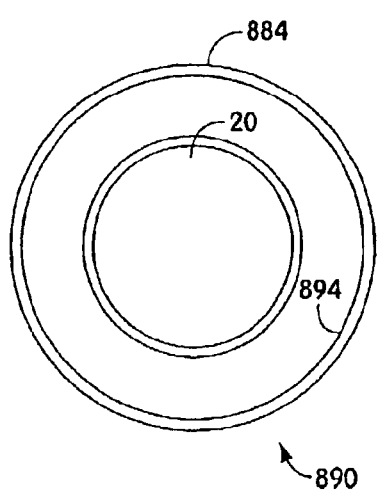
Fig. 21A  Fig. 21B

ENDOSCOPIC ACCESSORY ATTACHMENT MECHANISM

This application claims the benefit of Provisional Application No. 60/204,155, filed May 15, 2000.

FIELD OF THE INVENTION

The present invention relates to mechanisms and methods for attaching an endoscopic accessory component to a distal end of an endoscope.

BACKGROUND OF THE INVENTION

Endoscopic procedures provide a desirable, minimally invasive alternative to surgery in treating various internal ailments of the human body. Endoscopes comprise a long cylindrical tube having several channels or lumens, and can be inserted through a natural body lumen to an internal treatment site. Various procedures can be conducted by navigating instruments through the working channels of the endoscope. Frequently, viewing capability is provided through one of the channels of the endoscope to aid in conducting the procedure. Attachment of various accessory tools to the distal end of the endoscope that are remotely operable through a working channel of the endoscope and/or elements that track along the outside of the endoscope to the treatment site can broaden the range of procedures viable for endoscopic techniques. Accessory attachments for endoscopes are currently available to perform band ligation, mucosectomy and for endoscopic suturing and suture knot advancement. Such accessory devices must be securely attached to the distal end of the endoscope to prevent accidental release of the accessory in the patient potentially causing serious complications.

Presently available means for attaching such accessories to the distal end of an endoscope utilize a friction fit or set screws that are cumbersome for a physician to operate. Friction fit endoscopic attachment mechanisms comprise a cylindrical ring at the proximal end of the accessory device sized to fit tightly around the distal end of the endoscope. The close sizing and proper material selection provide frictional contact to hold the accessory onto the distal end of the endoscope. However, the close fitting high frictional engagement provided by the cylindrical attachment mechanism make loading the accessory onto the distal end of the endoscope cumbersome and time consuming. Additionally, the closely sized cylindrical component matches only one endoscope size and, therefore, different sizes of attachment mechanisms must be produced and kept on hand if different sized endoscopes are expected to be used.

Another type of attachment mechanism uses set screws threaded through an endoscopic accessory which push a movable shoe into tight engagement with the outside surface of the endoscope while another portion of the accessory device extends partially into the working channel of the endoscope to provide leverage against advancement of the set screw. Such an attachment mechanism has been used to secure an endoscopic suturing capsule as disclosed in U.S. Pat. Nos. 4,841,888, 5,037,021, 5,080,663, 5,792,153, all of which are incorporated herein by reference in their entirety. Although the movable shoe secured by the set screws provides a secure engagement for a range of endoscope sizes, it is cumbersome and time consuming for the physician to tighten the set screws to secure the device prior to the procedure.

It would be desirable to provide an endoscopic accessory attachment mechanism that securely attaches the accessory to the distal end of an endoscope and that can be applied easily and rapidly. It is an object of the present invention to provide such a mechanism and associated methods for its use.

It is noted that in the description of the present invention, "distal" refers to the direction along the device pathway leading internally to the patient and "proximal refers to the direction leading externally from the patient.

SUMMARY OF THE INVENTION

The present invention provides an endoscopic accessory attachment mechanism that utilizes a bracing member, a ramp surface and, preferably, a wedge slidable on the ramp surface to apply a compressive engagement force on surfaces of the distal end of an endoscope to secure the accessory. The engagement force is created by compression of the distal end of the endoscope between the bracing member and the ramp and wedge elements. The ramp's surface permits the compressive force applied to the endoscope to be adjustable so that the accessory can be applied to the distal end of the endoscope easily, then tightened. The addition of the wedge element, slidable on the ramp surface enhances the adjustability of the compressive engagement force, provides a secure engagement pad by it s top surface to contact the exterior of the endoscope and may provide a self-locking feature depending on the orientation of the ramp surface. The ramp surface also permits variability in the outside diameter of the endoscope to which the device is secured.

The attachment mechanism may be incorporated as part of the endoscopic accessory configured to be utilized at the distal end of the endoscope. Alternatively, the mechanism may be assembled to the accessory in a secondary operation such as adhesive bonding or riveting. Also the mechanism may be separate, but releasably engageable with the accessory. The mechanism may be configured as a coupling, configured as described herein to engage the endoscope at one end with the other end engaged as necessary to connect to an existing endoscopic accessory device. The mechanism does not interfere with the use of the channels and features of the endoscope and does not damage the surfaces of the endoscope by its attachment. The attachment mechanism can accommodate a range of commonly used endoscope diameter sizes, for example, such as scope diameters between 9.2 to 9.8 mm, providing the same secure engagement with each. However it is noted that the securement device of the present invention is equally applicable to and can be configured to correspond to endoscopes of larger or smaller sizes or catheters. To accommodate endoscopes that are significantly smaller or larger than the most common sizes, or to accommodate catheters, which are typically smaller and more flexible than endoscopes, the securement system can be made correspondingly larger or smaller to match the scale of the device in question.

The bracing member should be configured to lie in a plane that is parallel to the longitudinal axis of the endoscope as determined when the accessory is in the intended, attached position on the endoscope. The bracing member should be configured to engage a surface of the endoscope such as the outside surface of the scope or an internal surface such as the lumen wall of the working channel. In the case of engagement with the working channel, the bracing member may comprise a tube slidable within a small portion of the working channel. To engage the outer surface of the endoscope, the bracing member may be configured as a cylinder to encircle the entire circumference of the distal end of the endoscope or may take a form of a partial cylinder to engage only a fractional arc length of the circumference of the distal end of the endoscope.

The ramp surface is configured to project proximally past the distal face of the endoscope when the accessory is fully engaged with the endoscope. The ramp surface is inclined at an acute angle to the longitudinal axes of the endoscope and the bracing member. A forward facing ramp is defined when the angle of the ramp defines a rise that increases as the ramp projects proximally. With a forward facing ramp, an engagement force with the endoscope may be created as the accessory is slid proximally onto the distal end of the endoscope. With the proper spacing between the fixed bracing member and ramp surface, surfaces of the endoscope can be compressed between the ramp surface and bracing member as a force is applied to move the accessory relative to the endoscope in a proximal direction.

In a preferred embodiment, a wedge, slidable on the ramp surface is also provided with the mechanism to translate the engagement force from the ramp to a surface of the endoscope. A wedge facilitates application of the device to the endoscope, accommodates a varied range of endoscope sizes and may provide a self-locking feature, depending on the orientation of the ramp surface. The wedge, preferably, includes a top surface that serves as an engagement pad for contacting a surface of the endoscope. The bottom surface of the wedge is preferably inclined at an acute angle corresponding to the angle between the ramp surface and longitudinal axis of the endoscope. Therefore, as the bottom surface of the wedge slides in mated contact with the ramp surface, the top surface of the wedge will be parallel to the longitudinal axis of the endoscope and thus to the outside surface of the endoscope to facilitate secure engagement.

Using a wedge in combination with the ramp surface, the ramp may be oriented to be forward (as defined above) or reverse, such that the angle defines a rise that decreases in the proximal direction. The bottom surface of the wedge may have projecting guides that slide in keyways formed in the ramp surface to keep the wedge aligned as it slides on the ramp. Additionally, the wedge may be biased to one end of the ramp surface by a biasing member, such as one or more small coil springs. Biasing the wedge to its maximum range of travel on the highest part of the ramp helps to provide a self-locking feature for the system in that the wedge is maintained at the highest possible position on the ramp to provide the greatest compressive force on the surface of the endoscope at all times.

In use, a mechanism having a reverse ramp and biasing means to maintain the wedge at the proximal end (highest point) of the ramp would be applied as follows. The accessory is engaged with the distal end of the endoscope, being slid proximally so that the bracing member engages the intended surface of the endoscope and the top surface of the wedge engages the outside surface of the endoscope. As the device is pushed proximally, the wedge slides down the ramp slightly to permit acceptance of the device onto the distal end of the endoscope. Additionally the wedge may have a beveled edge to aid in engaging and sliding under the advancing endoscope. Once the device is sufficiently advanced onto the endoscope, the wedge will be biased to the highest possible point on the ramp by a biasing means. A backstop at the distal end of the ramp that remains distal to the distal end of the endoscope indicates to the user the extent to which the device has been loaded onto the endoscope. Flush engagement between the distal face of the endoscope and backstop is not necessarily required for secure mounting.

A separate leverage tool may be provided so that the user can engage the wedge directly to apply an additional longitudinal force to drive the wedge further up the ramp, increasing the compressive force on the surfaces of the endoscope, now locked between the bracing member and the wedge. Not only is secure engagement achieved initially, but any force acting to move the accessory distally relative to the endoscope (a removal direction) tends to cause the wedge to be dragged further up the ramp due to its frictional engagement with the surface of the endoscope. As the wedge is dragged further up the ramp, compressive force on the endoscope continues to increase to resist the distal removal force. The effect of dragging the wedge further into locking engagement during application of a distal force is enhanced by the use of highly frictional materials in the components, such as hard rubber. Use of stainless steel or other rigid materials may reduce the self-locking effect with the reverse ramp configuration.

In the case of a forward facing ramp configuration, the wedge also slides along the surface to provide a greater clearance distance between the bracing member and wedge to permit installation of the device onto a distal end of an endoscope then permits sliding of the wedge to the high point of the ramp to reduce the clearance between the bracing member and wedge and creates compressive force on the endoscope and lock the device. Biasing members may also be used in the forward ramp embodiment. However, the wedge must be maintained at its distal most limit of travel along the ramp at which point would occur the highest compressive force on the endoscope. Because proximal movement of the wedge from this point on the ramp would serve to reduce the compressive force on the endoscope, the forward ramp embodiment does not provide a self-locking attribute of the ramp embodiment. Specifically, as a removal force is applied to the accessory in the distal direction relative to the endoscope, the wedge, by its frictional engagement with the surface of the endoscope, would be dragged proximally, down the ramp, reducing compressive loading on the endoscope. However, frictional engagement of the ramp against the surface of the endoscope is sufficient to provide a locked engagement capable of withstanding removal forces.

In another alternative embodiment of the invention, the attachment mechanism may comprise a separate wedge element that is independently loadable onto the distal end of the endoscope and a ramp cone attached to the accessory that is engageable over the cylindrical wedge. The wedge may comprise an annulus having a cross-sectional shape of a wedge, having a flat inside surface that is parallel to the longitudinal axis of the endoscope and a sloped outside surface at an acute angle to the longitudinal axis of the endoscope. As with the previous embodiments, the ramp surface created by the cone and the sloped surface of the wedge may be oriented to be forward or reverse. However, as in the embodiments described above, the reverse ramp configuration provides a self-locking feature, when a pliable wedge material is used, such that a moving force applied to the accessory in a distal direction causes the ramp surface of the cone to push against the slope of the wedge causing compression and increased engagement force on the surface of the endoscope.

It is an object of the present invention to provide an endoscopic accessory attachment mechanism that can be easily and expeditiously used to securely fasten an accessory to a distal end of an endoscope.

It is another object of the invention to provide an endoscopic accessory attachment mechanism that increases locking force with the endoscope as a removal force acting to separate the accessory from the endoscope is applied.

It is another object of the invention to provide an endoscopic accessory attachment mechanism that utilizes the engagement between a ramp surface and a slope of a wedge to provide an adjustable engagement force with an endoscope that compresses the endoscope between the wedge and a bracing member.

It is another object of the invention to provide an endoscopic accessory attachment mechanism that accommodates a range of endoscope or catheter sizes.

It is another object of the invention to provide an endoscopic accessory coupling, engageable with the distal end of an endoscope at one end and engageable with an accessory at its other end.

It is another object of the invention to provide a method of securing an endoscopic accessory to a distal end of an endoscope that requires a minimum of steps and results in secure engagement of the accessory.

It is another object of the invention to provide a method of securing an endoscopic accessory to a distal end of an endoscope that utilizes the compressive force exerted on an endoscope by two surfaces of the accessory for securement.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 11 is a side view of an endoscopic accessory comprising the ramp surface, wedge and bracing member with the wedge at the top of the ramp surface;

FIG. 12 is a side view of an endoscopic accessory comprising in a locked position;

FIGS. 13A–D present, in side view, a series of stages of the endoscopic accessory comprising the attachment mechanism of the present invention being loaded onto a distal end of an endoscope; and a side view of an endoscopic accessory being loaded onto a distal end of an endoscope

FIG. 20A is a side view of an alternate embodiment of the endoscopic accessory attachment mechanism comprising a funnel shaped ramp surface and a separable annular wedge;

FIG. 20B is an end view of an alternate embodiment of the endoscopic accessory attachment mechanism comprising a funnel shaped ramp surface and a separable annular wedge;

FIG. 21A is a side view of an alternate embodiment of the endoscopic accessory attachment mechanism comprising a funnel shaped ramp surface and a separable annular wedge;

FIG. 21B is an end view of an alternate embodiment of the endoscopic accessory attachment mechanism comprising a funnel shaped ramp surface and a separable annular wedge;

DESCRIPTION OF THE ILLUSTRATIVE EMBODIMENTS

Figure 1:
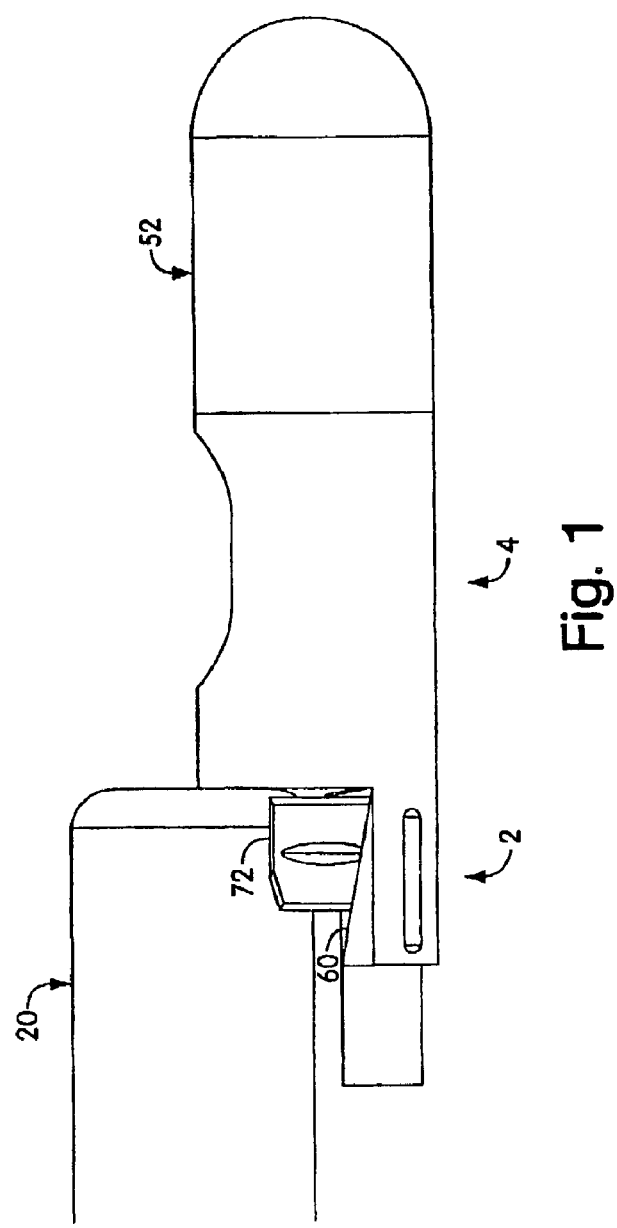
FIG. 1 is a side view of a preferred embodiment of the endoscopic accessory attachment mechanism engaged with an endoscope.
Figure 2:
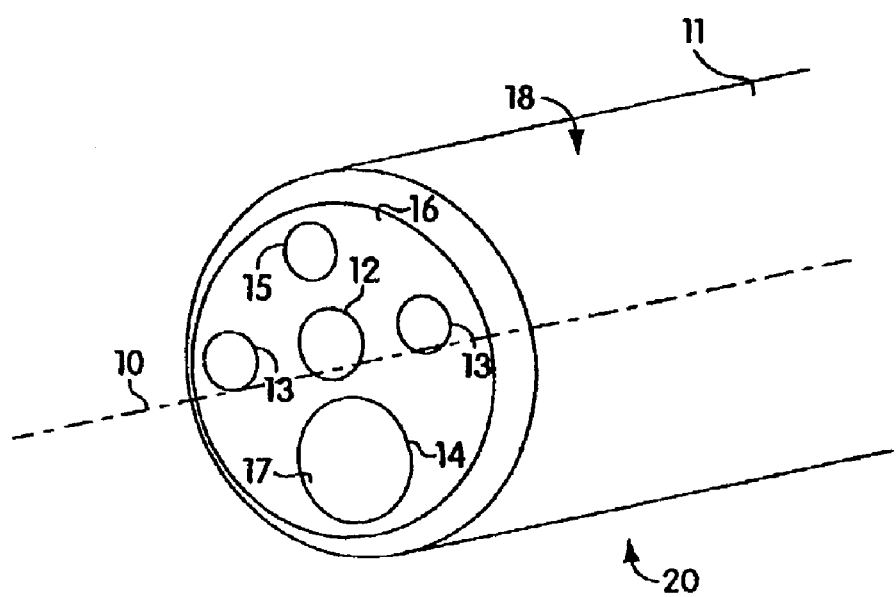
FIG. 2 is an isometric view of a distal end of a typical endoscope having viewing capability.

The present invention provides an endoscopic accessory attachment mechanism 2, which may be incorporated into an endoscopic accessory 4 to provide secure attachment to the distal end of an endoscope 20, as is shown in FIG. 1. The principles of the attachment mechanism may be applied equally well to catheter devices, though the invention is explained in this description in the context of endoscopes. The primary components of the mechanism are a ramp surface 60, a wedge 72 and a bracing member 92 (shown in FIGS. 11–13). FIG. 2 shows the distal end 18 of a flexible endoscope 20 with which the present invention may be used. Terminating at the distal face 16 of the endoscope are several channels through which various functions may be performed. Typically, at least one large working channel lumen 14 is provided through which various medical instruments, catheters or accessory control mechanisms may be passed. In the case of viewing endoscopes, a viewing lens 12 is provided on the distal face of the endoscope to permit viewing via optical fiber or digital electronics that extend from the lens through the endoscope to its proximal end and attach to viewing equipment external to the patient. Lights 13 illuminate the treatment site so that it may be viewed through the lens 12. Some endoscopes also have a fluid port 15 through which solution may be passed under pressure to rinse the lens of biological material during a procedure.

As mentioned above, the endoscopic accessory attachment of the present invention may be integrated with any type of endoscopic accessory. Examples of procedures that can be performed by accessory devices attached to a distal end of an endoscope include band ligation, mucosectomy or endoscopic suturing for the treatment of such maladies as gastroesophageal reflux disease, among others.

Figure 3:
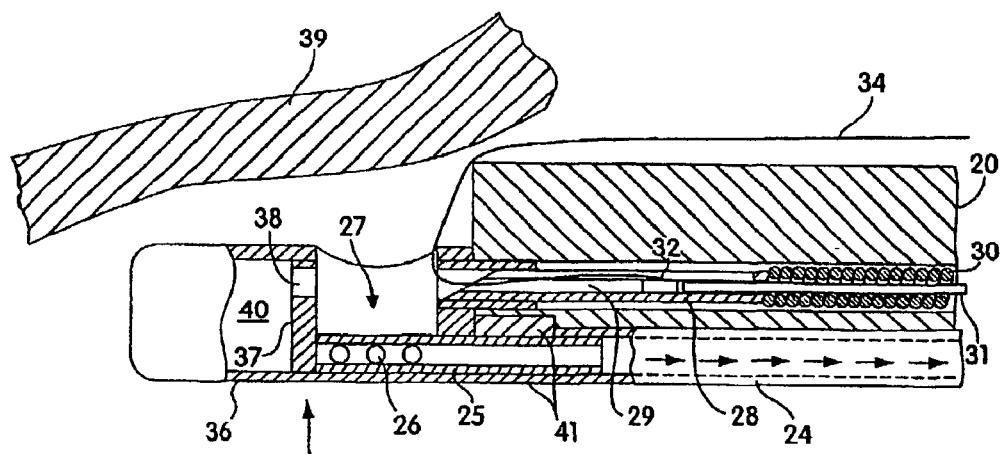
FIG. 3 is a partial sectional side view of a prior art endoscopic suturing accessory.
Figure 4:
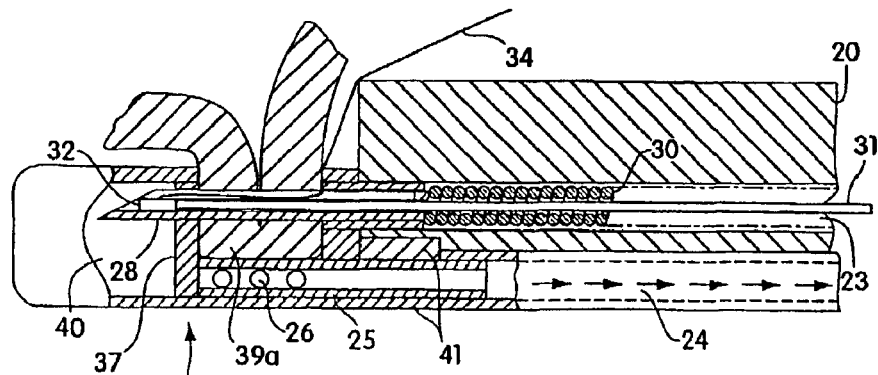
FIG. 4 is a partial sectional side view of a prior art endoscopic suturing accessory.
Figure 5:
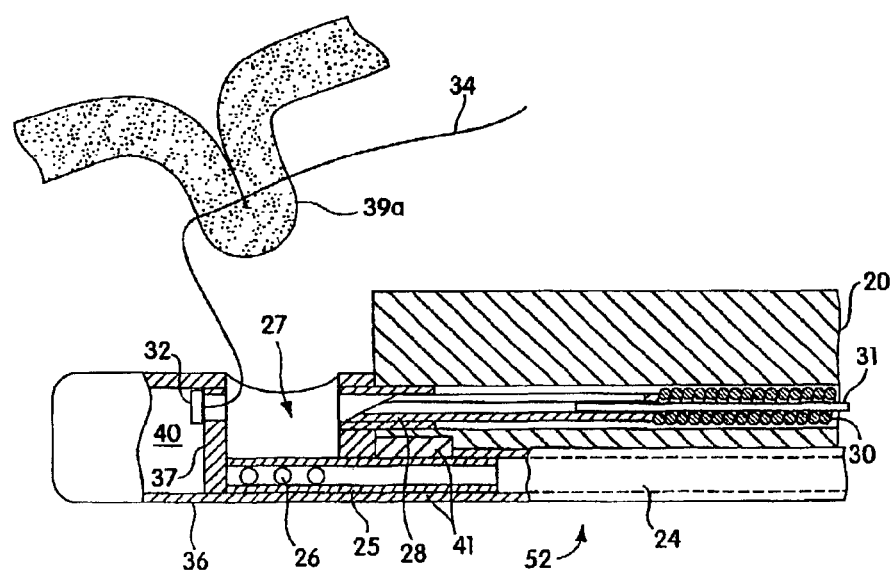
FIG. 5 is a partial sectional side view of a prior art endoscopic suturing accessory.

To illustrate an example of an endoscopic accessory, FIGS. 3–5 depict a prior art endoscopic suturing device disclosed in U.S. Pat. No. 5,792,153. FIG. 3 shows the distal end of a flexible endoscope 20, on which a sewing device 52 is attached. As mentioned above, the endoscope is provided with a viewing channel, which is not shown, but which terminates at a lens 12 on the distal face of the endoscope (FIG. 2). The endoscope is further provided with a biopsy channel 14, and a suction channel 24 the proximal end of which is connected to a source of reduced pressure (not shown). The sewing device 52 has a tube 25, which communicates with the suction pipe 24 and has a plurality of perforations 26 therein. These perforations communicate with an upwardly open cavity 27 formed in the sewing device.

A hollow needle 28 is mounted in the biopsy channel 14, with its beveled tip extending into the sewing device. The needle has a channel 29 extending therethrough. A flexible, wire-wound cable 30 has its forward end attached to the rear of the needle 28, and a center wire 31 runs within the cable 30, along the entire length thereof, and is longitudinally movable with respect thereto. The diameter of the wire 31 is such that it is longitudinally movable within the channel 29 and, in the position shown in FIG. 3, the distal end portion of the wire 31 extends into the proximal end portion of the channel 29.

Figure 3A:
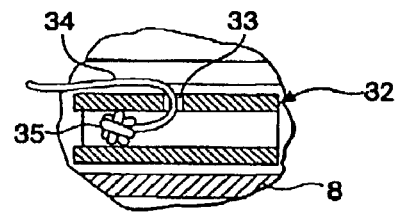
FIG. 3A is a detailed view of the suture tag shown in FIG. 3.

A thread carrier in the form of a tag 32 is mounted in the channel 29. The tag is shown in more detail in an enlarged view, shown in FIG. 3A. The tag may be hollow and has an aperture 33 extending through the sidewall thereof. As can also be seen in FIG. 3, one end of a thread 34 is secured to the tag by passing it through the aperture 33 and tying in the end of a knot 35 of sufficient size to prevent the thread escaping from the tag.

The sewing device accessory has a hollow head portion 36 defining a chamber 40 therein, distal to the cavity 27. Between the chamber 40 and the cavity 27 is a wall 37, in which there is formed an aperture 38. The aperture 38 has a diameter that is marginally greater than the external diameter of the needle 28, and is aligned therewith. The clearance between the needle 28 and the aperture 38 must be sufficiently small to prevent tissue being forced through the aperture and causing the needle to jam. Finally, FIG. 3 shows a portion of the patient's tissue 39, in which a stitch is to be formed.

In operation, suction is applied to the suction pipe 24, and thus, to the cavity 27 via communication through the perforations 26 in the tube 25. The suction aspirates into the cavity a U-shaped portion 39a of the tissue 39, as shown in FIG. 4. The hollow needle 28 is pushed through the U-shaped tissue portion 39a by exerting a leftwards force on the wire-wound cable 30, and the tag 32 is pushed along the channel 29 from right to left, by exerting a leftwards force on the center wire 31. After full advancement of the needle, the tip portion of the needle 28 is on the left-hand side of the wall 37, within the chamber 40 in the hollow head portion 36, and the tag 32, within the channel 29, lies to the left of the wall 37.

Continued leftwards movement of the wire 31 pushes the tag 32 out of the channel 29 and into the chamber 40. The wire 31 is then withdrawn rightwardly, followed by rightward withdrawal of the cable 20, to bring both back to the positions which they occupy in FIG. 3. The suction is then discontinued so allowing the U-shaped tissue portion 39a to be released from the cavity 27. The position of the components is then as shown in FIG. 5. Finally, the endoscope and sewing device are withdrawn from the patient. In so doing, the thread 34 is pulled partially through the tissue portion 39a, since the tag 32 is trapped in the chamber 40. The end result is that both ends of the thread are outside of the patient and can be knotted and/or severed as may be appropriate. It should be noted that a multiple stitch embodiment also is disclosed in U.S. Pat. No. 5,792,153.

Figure 6:
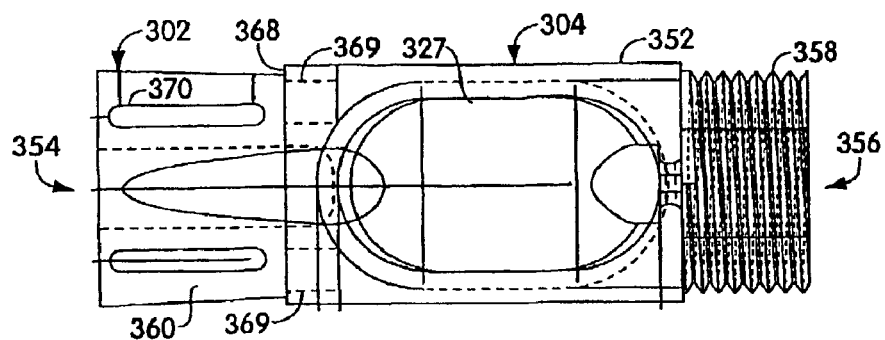
FIG. 6 is a top view of an endoscopic accessory comprising the ramp surface of the endoscopic attachment mechanism.
Figure 7:
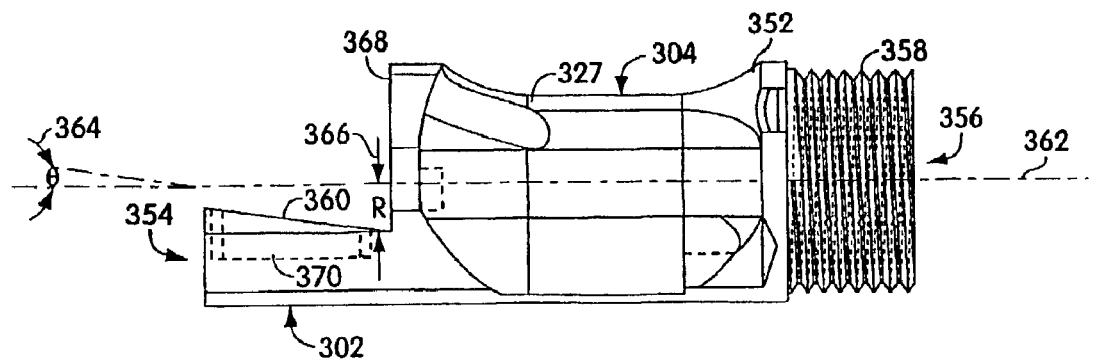
FIG. 7 is a side view of an endoscopic accessory comprising the ramp surface of the endoscopic attachment mechanism.

FIG. 6 shows a top view of an endoscopic accessory comprising a suture capsule body 352 similar to the prior art device described above, but employing an attachment mechanism of the present invention. FIG. 7 shows a side view of the endoscopic suture capsule 352. The suture capsule may be machined and assembled from a rigid material such as stainless steel or a polymer and comprises a proximal end 354 and a distal end 356. The distal end of the capsule body may include threads 358 to threadably receive a cap (not shown), similar to cap 36 described above. The capsule also comprises a cavity 327 into which is sucked a portion of tissue to be sutured as is described above. At the proximal end of the capsule body is formed, the attachment mechanism 302, which serves to secure the capsule to the distal end of an endoscope. FIGS. 6 and 7 show one component of the attachment mechanism: a ramp surface 360. The ramp surface lies in a plane, which is at an acute angle 364 to the longitudinal axis 362 of the endoscopic accessory 304. In the example of the suturing capsule body 352, the capsule is intended to be mounted to the distal end of the endoscope such that its longitudinal axis 362 is parallel to the longitudinal axis of the endoscope. Immediately proximal to the ramp surface 360 is a backstop 368 against which rests the distal face 16 of an endoscope when fully engaged with the accessory 304. However, flush engagement with the backstop may not be necessary to achieve adequate engagement.

Figure 8:
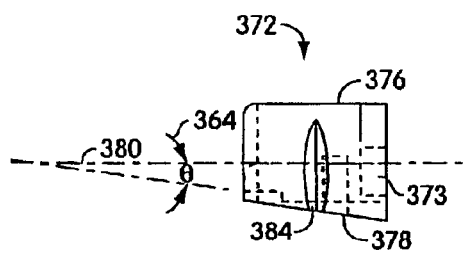
FIG. 8 is a side view of the wedge of the present invention.
Figure 9:
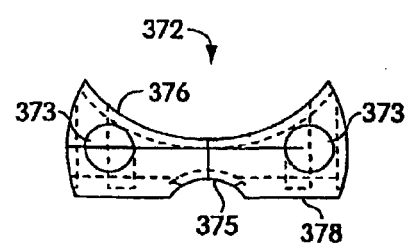
FIG. 9 is a front view of the wedge of the present invention.
Figure 10:
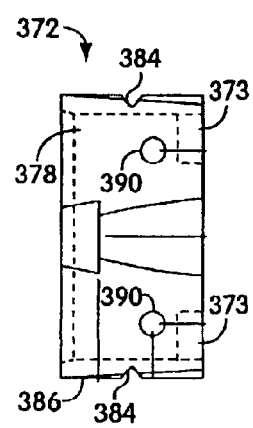
FIG. 10 is a bottom view of the wedge of the present invention.
Figure 10A:
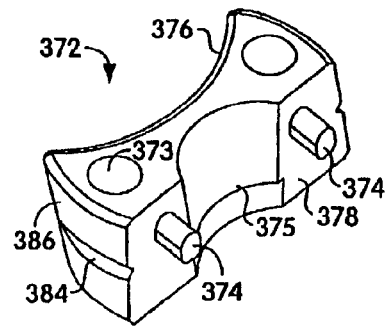
FIG. 10A is an isometric view of the wedge of the present invention.

The ramp surface 360 has one or more keyways 370 to receive projections 374 of a wedge 372 which is slidable on the ramp surface to transmit compressive force to a surface of an endoscope such as the outside surface 11 (FIG. 2). FIG. 8 shows a side view of the wedge 372. FIG. 9 is a front view of the wedge, FIG. 10 is a bottom view and FIG. 10A is an isometric view of the bottom of the wedge. The wedge normally resides atop the ramp surface 360 of the attachment mechanism 302, but is shown separately in these figures to illustrate the features of this component.

The wedge comprises a top surface 376, which is parallel to the longitudinal axis 380 of the wedge. The wedge also includes a bottom surface 378, which is oriented at an acute angle 364 to the longitudinal axis 380 of the wedge. When the bottom surface 378 is in mating engagement with the ramp surface 360, both inclined at an acute angle θ 364, the top surface 376 of the wedge remains parallel to the longitudinal axis of the endoscope and thus the outside surface of the endoscope 11. The top surface 376 has a curved shape to match the arc of the outside surface 11 of the endoscope as is best seen in FIG. 9. So shaped, the top surface 376 acts as an engagement pad for contacting the endoscope surface and applying compressive force without damaging the surface of the endoscope. Alternatively, the wedge may have a top surface that is rounded so that only an arc shaped line contacts the endoscope.

Spring guide holes 373 are formed into the front face 382 of the wedge to hold and restrain biasing members such as small coil springs 348. Additionally, the wedge includes engagement ridges 384 etched into the side surfaces 386 of the wedge. The engagement ridges are arranged to coincide with projections on an optional, separate loading tool to permit the operator to apply a longitudinal force to the wedge only to adjust force applied to the endoscope surface. In the endoscopic suturing capsule, body 352, a suction tube 25 is required to provide a vacuum source to the cavity 27. Because this suction tube 25 extends through the ramp surface area, the bottom surface 378 of the wedge 372 has a crescent shape contour 375 cut-out to provide clearance for the suction tube 25. However, such a crescent contour 375 would not be required in embodiments where a suction tube was not used. Additionally, projections 374 protrude from the bottom surface 378 of the wedge to ride in keyways 370 formed into the ramp surface. The projections and keyways help to maintain the wedge aligned as it slides on the ramp or up and down the ramp surface 360. The projections may be fitted into projection receptacles 390 formed into the bottom surface of the wedge.

FIGS. 11 and 12 show side views of the endoscopic accessory 304, specifically a suturing capsule body 352 comprising all components of the attachment mechanism in their operational relationships. A bracing member 392 extends proximally from the capsule body 352 to engage a surface of the endoscope. The bracing member has a longitudinal axis 394 that is parallel to the longitudinal axis of the endoscope 10 and longitudinal axis of the capsule 362 and wedge 380. In the example shown in FIG. 11, the bracing member 392 comprises a tube that is receivable within a portion of the working channel 14 of an endoscope. The bracing member, in this instance, has a lumen 396 to permit passage of instruments or controls through the working channel of the endoscope into the endoscopic accessory 304, such as the needle 28 and suture tag 32 of the endoscopic suturing device discussed in detail above.

Figure 13A:
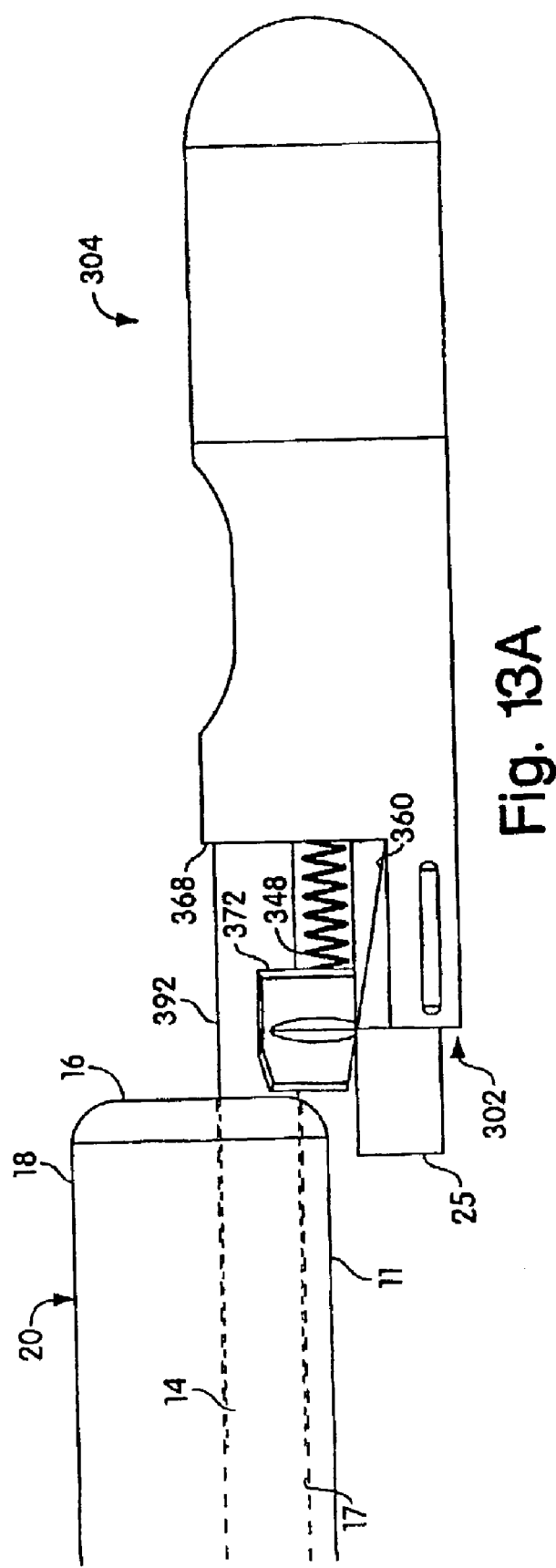
Figure 13C:
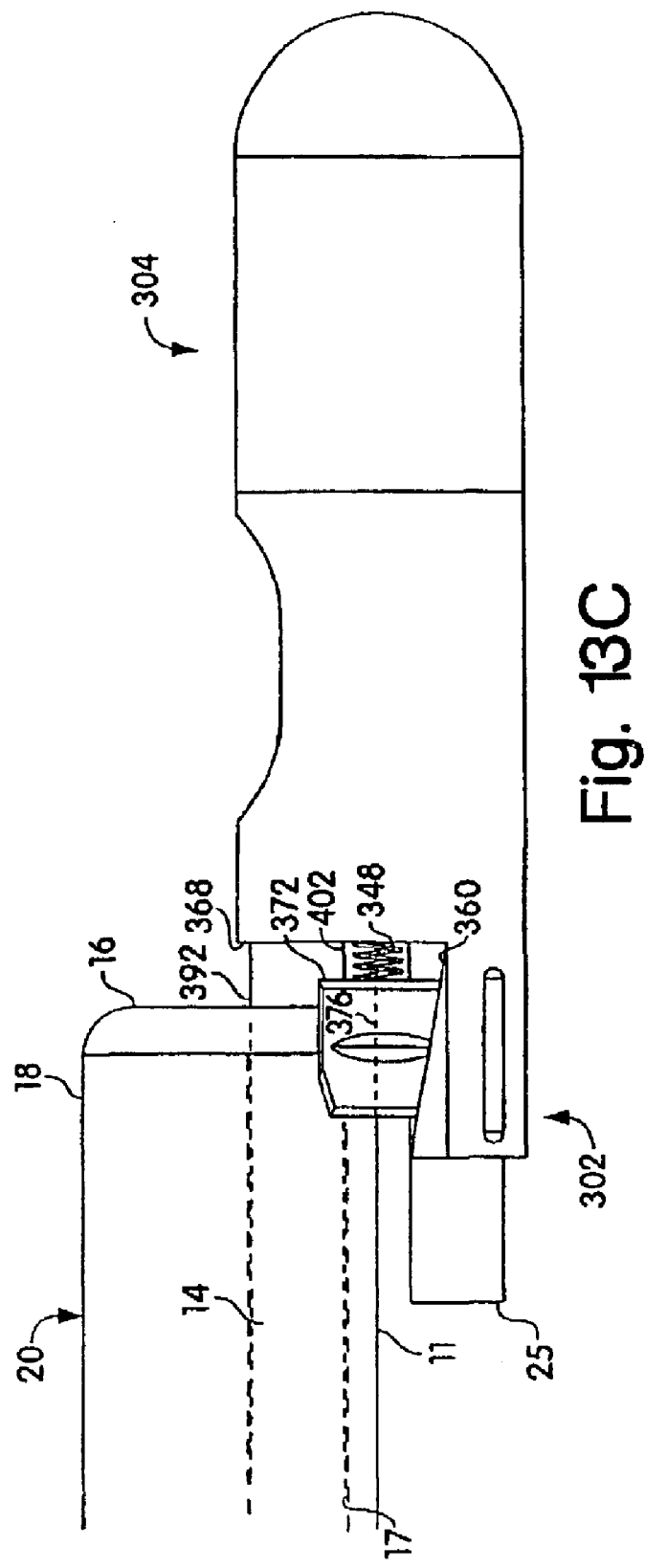

As the wedge 372 slides up the ramp surface 360 from a loading position to a locked position at the top of the ramp surface 360, as shown in FIG. 12, the distance D 398 between the top surface 376 of the wedge and the bottom surface 402 of the bracing member decreases to capture and apply a compressive force to a portion of an endoscope captured therebetween. In a first position wherein the wedge is located at the bottom of the ramp surface as is shown in FIG. 11, a distance D 398 exists between the bottom surface 402 of the bracing member and the top surface 376 of the wedge 372. In this position, there is sufficient clearance for a portion of a distal end of an endoscope to slide therebetween so that the accessory 304 can be mounted to its distal end. In a second position wherein the wedge 372 is positioned at the top of the ramp surface 360, as shown in FIG. 12, a reduced distance d 400 exists between the bottom surface 402 of the bracing member and the top surface 376 of the wedge. In this position, the surfaces 402 and 376 engage working channel surface 17 and outer surface 11, of the endoscope, tightly capturing the endoscope and locking the accessory 304 to its distal end FIGS. 13A–13D show progressive steps of loading an endoscopic accessory 304 onto a distal end 18 of an endoscope 20 using the attachment mechanism 302 of the present invention. In FIG. 13A, the bracing member 392 is inserted into the working channel 14 at the distal end 18 of an endoscope 20. Initially, biasing members, such as small coil springs 348 maintain the wedge 372 at the top of the ramp surface 360. In FIG. 13B, the accessory 304 is moved more proximally with respect to the distal end of the endoscope. The bracing member 392 continues to travel further inside the working channel 14 of the endoscope and the distal face of the endoscope 16 begins to contact the wedge member 372. A slight beveled edge 406 at the proximal end 408 of wedge 372 may be provided to help guide the distal end of the endoscope onto the top surface 376 of the wedge. Because of the floating arrangement of the wedge 372 on ramp surface 60, the wedge may be adjusted and rotated slightly around the peak 410 of ramp surface 360 to additionally facilitate loading of the distal end of the endoscope onto top surface 376. As shown in FIG. 13C, as the accessory is pushed proximally relative to the distal end of the endoscope, the wedge 372 is pushed distally to travel down the ramp 360, thereby increasing the distance between the top surface of the wedge 376 and the bottom surface of the bracing member 392 to provide adequate clearance to accept the endoscope therebetween. Springs 348 become compressed as the wedge slides down the ramp 360 and increasing amounts of potential energy is stored in them to force the wedge 372 back proximally up the ramp to maintain a contact fit between the endoscope surface 11 and top surface 376 of the wedge.

FIG. 13D shows the accessory 304 and endoscope 20 after loading has been completed. The distal face 16 of the endoscope abuts the backstop 368 of the accessory 4, bracing member 392 is fully inserted into working channel 14 and bottom surface 402 of bracing member 392 engages lumen surface 17 of the working channel. The presence of the bracing member within working channel 14 and the engagement of the surfaces presents a compressive force created by upper top surface 376 of wedge 372, resiliently pushed into engagement with endoscope surface 11 by springs 348, which bias the wedge up the ramp 360. In this position, sufficient frictional contact between surfaces of the attachment mechanism 302 and surfaces of the endoscope 20 exist to hold the accessory 304 in place at the distal end 18 of the endoscope. It is important to note that the distal face 16 of the endoscope need not necessarily abut the backstop 368 to be considered securely loaded onto the endoscope. The position of the wedge along the ramp surface at the point secure engagement is achieved may vary depending on the diameter of the scope or catheter in question. In this sense, the ramp arrangement provides a securement mechanism that can accommodate a variety of scope sizes.

Figure 14:
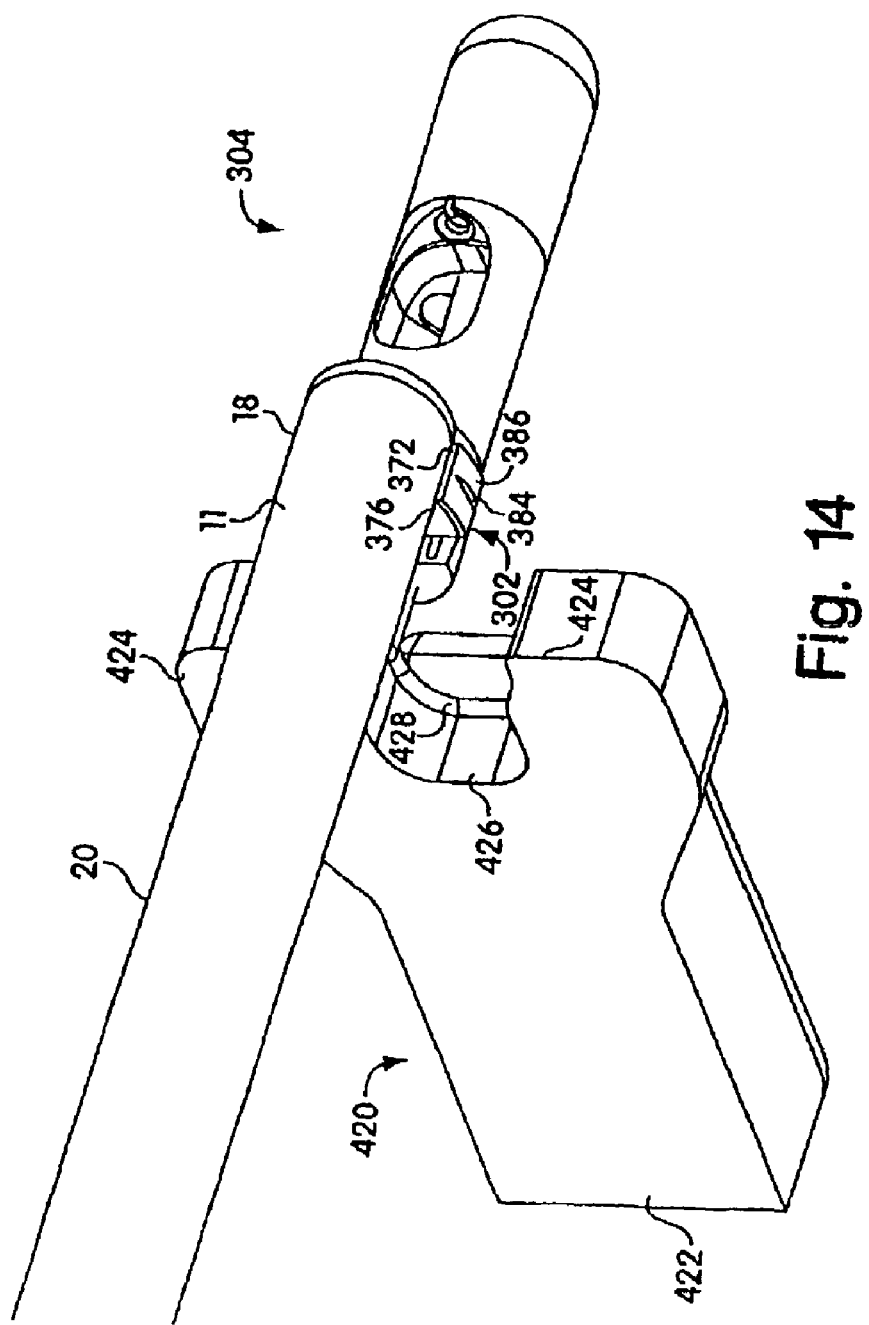
FIG. 14 is a diagrammatic illustration of a leverage tool being applied to the attachment mechanism to provide manual sliding and locking of the wedge.

FIG. 14 demonstrates the use of a loading tool 420 in securing the wedge into firm engagement with the outer surface 11 of the endoscope. The Y-shaped tool 420 comprises a handle 422 (at the base of the Y shape). Two forks 424, which surround the attachment mechanism 302 between the forks 424, U-shaped recess 426 is defined having an engagement ridge 428 that interlocks with the engagement groove 384 defined on the side surface 386 of the wedge 372. After the accessory 304 has been advanced proximally as far as possible relative to the endoscope during mounting, the user can position the tool such that engagement ridge 428 interlocks with engagement groove 384. The user then can apply a longitudinal force on the wedge 372 in a proximal direction through the tool 420 to insure that the wedge has been displaced as far as possible up the ramp to apply a secure compressive force against the outside surface 11 of the endoscope.

Figure 15:
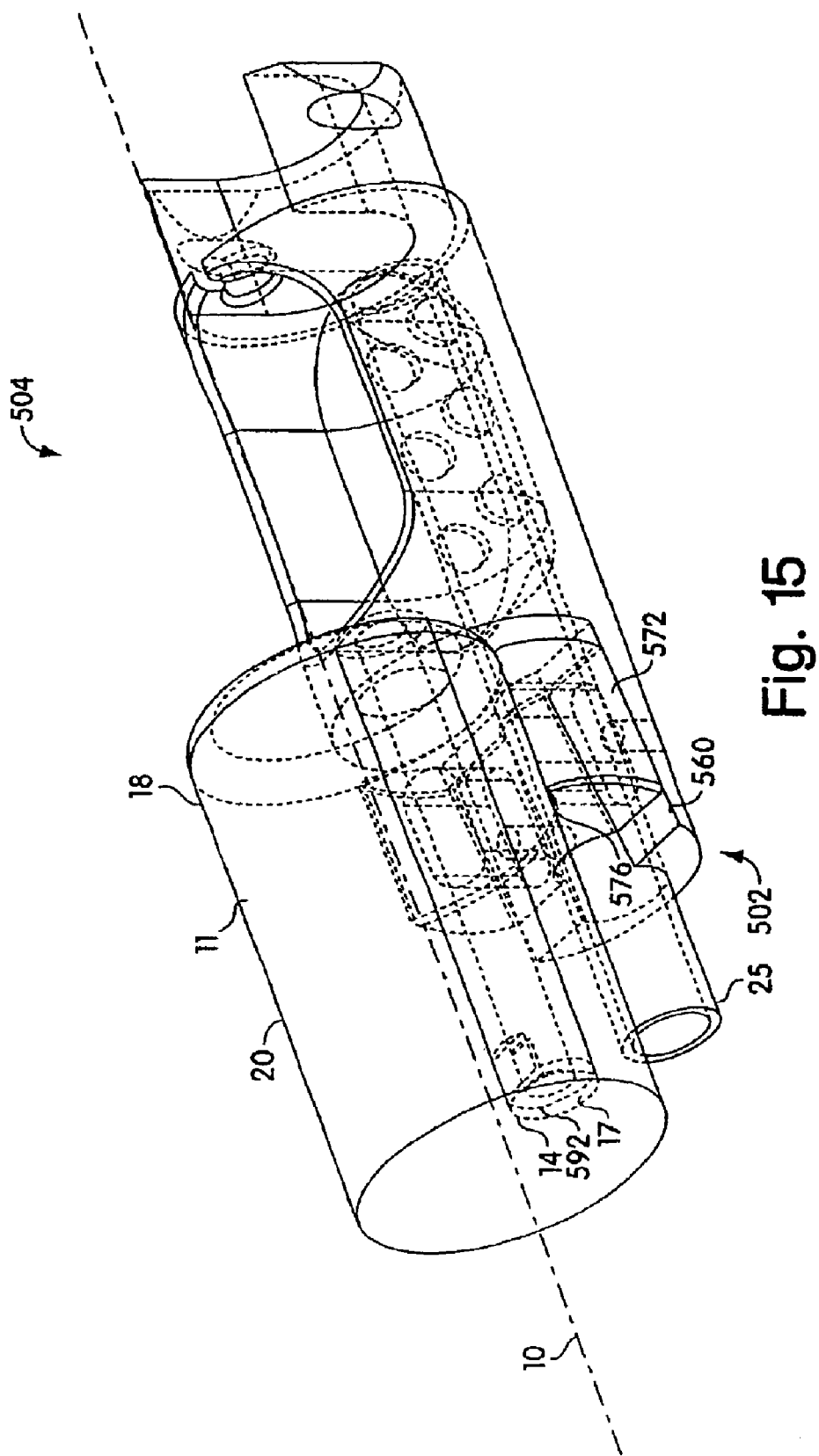
FIG. 15 is an isometric skeletal view of an alternate embodiment of the present invention utilizing a forward facing ramp surface.
Figure 16A:
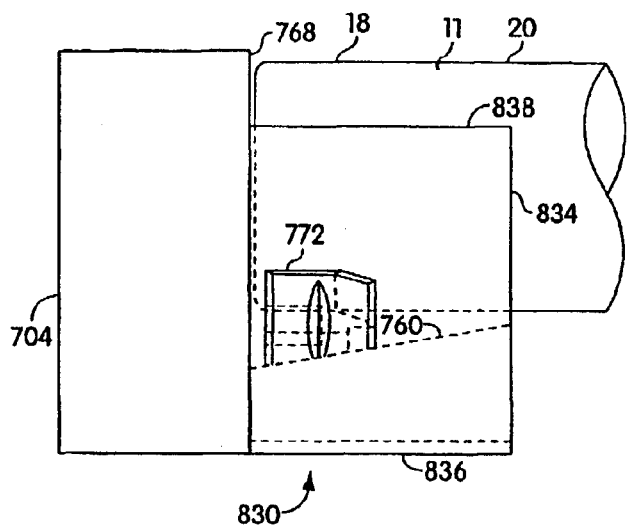
FIG. 16A is a side view of an alternate embodiment of the endoscopic accessory attachment mechanism comprising a semicircular bracing member.
Figure 16B:
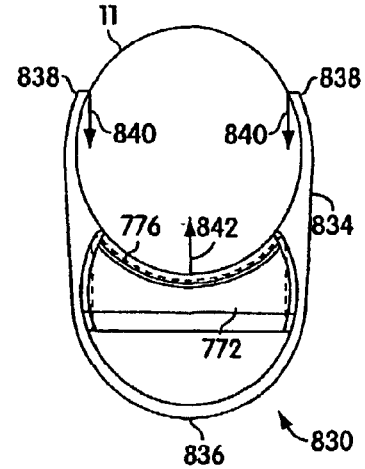
FIG. 16B is an end view of the alternate embodiment of the endoscopic accessory attachment mechanism comprising a semicircular bracing member.

FIG. 15 shows an alternate embodiment 502 of the attachment mechanism having a forward facing ramp 560. The ramp surface 560 is forward facing in the sense that the acute angle that the ramp forms with the longitudinal axis of the endoscope 10 defines a rise R (as shown in FIG. 7) that increases in the proximal direction (the opposite direction from the reverse ramp embodiment described above). In use, after the accessory body 504 is loaded onto the distal end 18 of the endoscope 20, the wedge 572 is affirmatively slid up the ramp 560 (in a distal direction) to bring the top surface 576 of the wedge into firm contact with the outside surface 11 of the endoscope. The compressive force created by the top surface of the wedge is opposed by the bracing member 592 residing in working channel 14, in contact with working channel lumen surface 17.

As shown in FIGS. 16–21B, the bracing member need not be inserted into the working channel of the endoscope to engage the inside surface 17 of the working channel lumen in order to brace the force provided by the wedge 772 on the outside surface of the endoscope. Alternate embodiments of the attachment mechanism have a bracing member configured to engage a portion of the outside surface of the endoscope 11 as well as, but in an orientation that opposes the force provided by the wedge 772. FIG. 16A is a side view of an alternate embodiment of the attachment mechanism comprising such a bracing member and accessory 704. The attachment mechanism 830 comprises the same arrangement of ramp surface 760 and wedge 772 as in the previous embodiments but substitutes a bracing member 838 that comprises a C-shaped band 834. As shown in FIG. 16A and the corresponding end view as shown in FIG. 16B, the C-shaped band curves around the bottom 836 of the attachment mechanism 830 and the ends 838 of the C-shaped band extend more than halfway around each side of the circumference of the endoscope to provide an opposing force 840 against the surface 11 of the endoscope in opposition to the upward force 842 resulting from engagement of the top surface 776 of wedge 772. The C-shaped band must necessarily be formed from a rigid polymer or stainless steel to provide the requisite rigidity to resist bending at the ends 838 as a result of the engagement force provided by the wedge 772.

Figure 17:
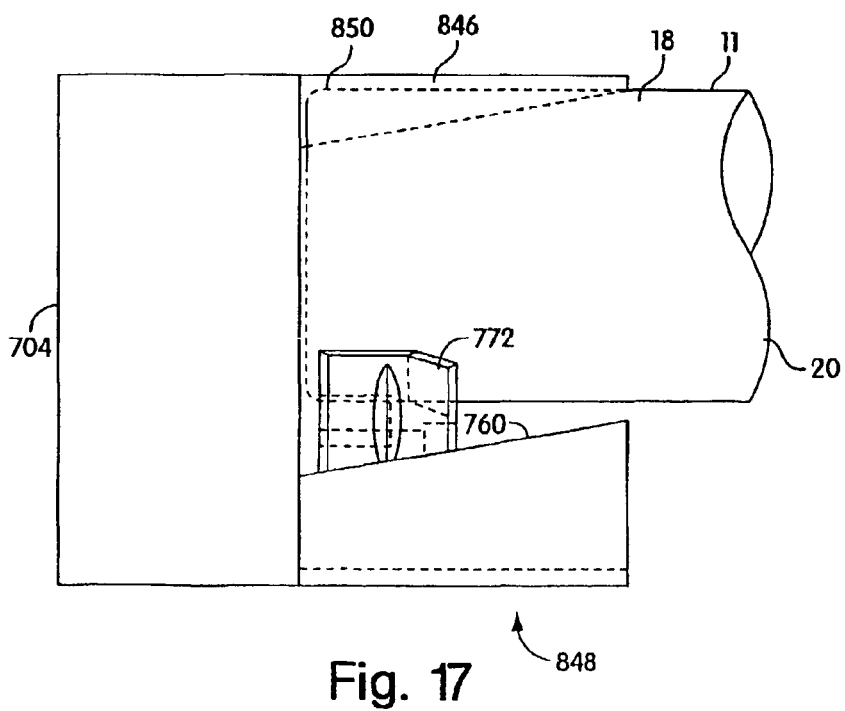
FIG. 17 is an alternate embodiment of the endoscopic accessory attachment mechanism comprising a visor-like bracing member.

FIG. 17 shows a side view of another alternate embodiment of the attachment mechanism 848. Like the alternate embodiment of FIGS. 16A and 16B, the bracing member engages the outside surface 11 of the endoscope to provide an opposing force to that generated by the wedge 772 as it is moved up the ramp surface 760. However, the engagement mechanism 848 realizes a bracing member 846 that extends proximally from the endoscopic accessory to engage the top 850 of the endoscope over a relatively narrow arc of its circumference, just sufficient to prevent the endoscope from slipping out of contact with the bracing member 846. The bracing member in this embodiment may have a visor shape to capture a sufficient arc length of the circumference of the top of the endoscope 850. The curved shape of the top surface 776 of the wedge 772 likewise provides engagement with an adequate arc length of the endoscope surface to prevent inadvertent disengagement from the attachment mechanism 848.

Figure 18A:
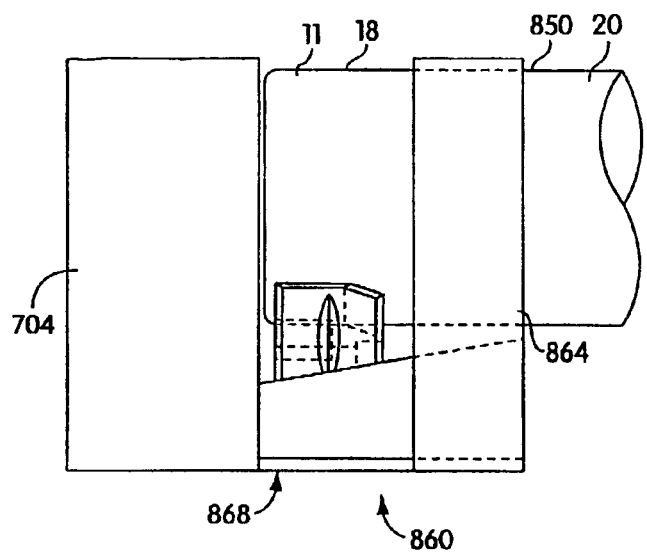
FIG. 18A is a side view of an alternate embodiment of the endoscopic accessory attachment mechanism comprising a short length circumferential bracing member.

FIG. 18A shows a side view of another alternate embodiment of the present invention wherein the bracing member 864 engages the outside surface of the endoscope 20. The attachment mechanism 860 comprises a bracing member 864 configured as a short length circumferential band that encircles the bottom of the engagement mechanism 868 and continues around the endoscope to encircle the top 850 of the endoscope as well.

Figure 18B:
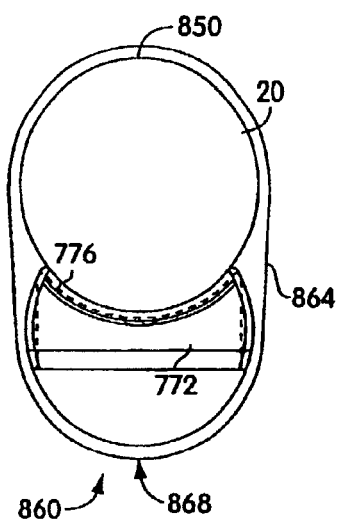
FIG. 18B is an end view of an alternate embodiment of the endoscopic accessory attachment mechanism comprising a short length circumferential bracing member.
Figure 19A:
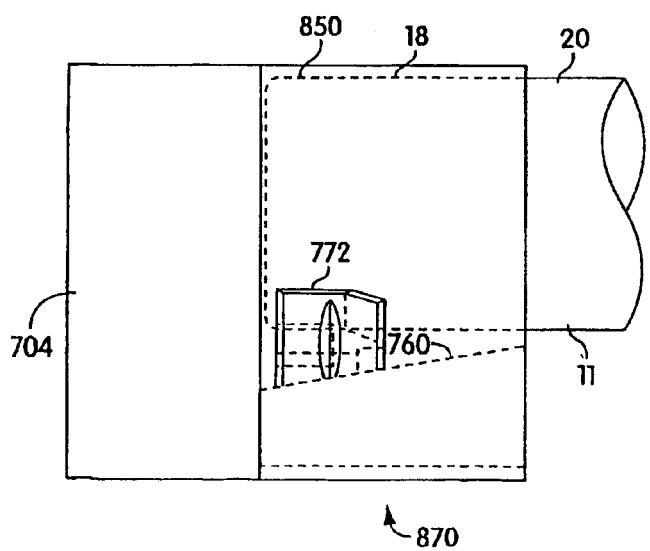
FIG. 19A is a side view of an alternate embodiment of the endoscopic accessory attachment mechanism comprising a long circumferential bracing member.
Figure 19B:
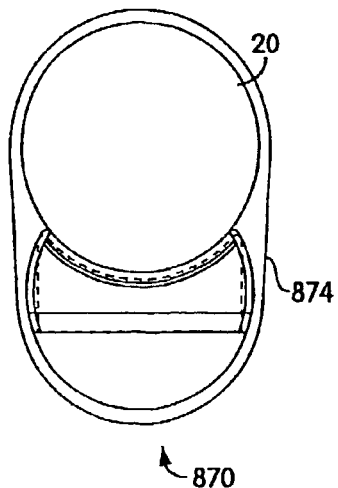
FIG. 19B is an end view of an alternate embodiment of the endoscopic accessory attachment mechanism comprising a long circumferential bracing member.

FIGS. 19A and 19B show an attachment mechanism 870 that is similar in configuration to that described in connection with FIGS. 18A and 18B. However, the circumferential band is of a longer length to contact greater surface area of the endoscope 20. The bracing member 874 comprises a cylindrical band, which encircles the ramp surface 760 and wedge 772 components of the mechanism and provides an opposing force at the top of the endoscope 850 to lock the accessory 704 onto the distal end of the endoscope. The embodiments of FIGS. 16A–19B may use biasing members fabricated from hard rubber, nylon or stainless steel and may be attached to attachment mechanism by adhesive, rivets or other suitable means.

FIGS. 20A and 20B show another alternate embodiment of the attachment mechanism 880 comprising a separate wedge element 882 that is independently loadable onto the distal end 18 of the endoscope and a circumferential ramp cone 884 attached to the accessory 704 that is engageable over the cylindrical wedge 882. The wedge may comprise an annulus having a cross-sectional shape of a wedge: a flat inside surface 886 that is parallel to the longitudinal axis 10 of the endoscope and a sloped outside surface 888 at an acute angle to the longitudinal axis of the endoscope. As with the previous embodiments, the ramp surface created by the cone 884 and the slope surface of the wedge may be oriented to be forward or reverse. However, FIGS. 21A and 21B show a cone and annular wedge embodiment 890 oriented in the reverse direction, such that rise defined by the acute angle created between the longitudinal axis 10 of the endoscope and the axis 898 of the cone ramp surface 894 increases in the distal direction. As in the preferred embodiment described above, the reverse configuration can help to provide a self-locking feature, when a pliable wedge material is used. In this instance a longitudinal force applied to move the accessory in a distal direction causes the ramp surface of the cone to push against the slope of the wedge causing compression and increased engagement force on the surface 11 of the endoscope.

Additionally, the embodiments of FIGS. 20A–21B demonstrate an alternative configuration for engaging an accessory device. Specifically, the distal end 900 of the cone in each embodiment comprises a straight portion 902 that may be configured with a universal fitting connectable to a wide range of endoscopic accessories. For example the straight portion of the cone may have internal threads on its inside surface 904 to threadably receive a line of endoscopic accessories having external threads of the same size. Alternatively, the accessory may be joined to the opening defined at the distal end of the cone 900 by a snap fit, friction fit or adhesive. In this manner, the attachment mechanism serves as a universal connector or coupling between an endoscope and accessory.

Preferred materials for the embodiments of FIGS. 20A–21B include hard rubber to increase the coefficient of friction between the annular wedge and the cone. However at least the straight portion 902 of the cone should be formed from a more rigid material such as stainless steel or a hard polymer to provide a surface into which threads may be formed.

It should be understood however, that the foregoing description of the invention is intended merely to be illustrative thereof and that other modifications, embodiments and equivalents may be apparent to those who are skilled in the art without departing from its spirit.

Having thus described the invention what we desire to claim and secure by Letters Patent is:

1. An endoscopic accessory attachment comprising:
   proximal and distal ends,
   a bracing member having a longitudinal axis engageable with at least one surface of an endoscope,
   a ramp surface that is at an acute angle to the longitudinal axis of the bracing member,
   a wedge slidable on the ramp surface to provide variable engagement force on a surface of the endoscope in opposition to that provided by the bracing member.

2. An endoscopic accessory attachment as defined in claim 1 wherein the angle of the ramp surface defines a rise relative to the longitudinal axis of the bracing member that increases in the distal direction.

3. An endoscopic accessory attachment as defined in claim 2 wherein the engagement force on the surface of the endoscope increases as a longitudinal force is applied to move the accessory longitudinally in a distal direction, relative to the endoscope.

4. An endoscopic accessory attachment as defined in claim 1 wherein the angle of the ramp surface defines a rise relative to the longitudinal axis of the bracing member that increases in the proximal direction.

5. An endoscopic accessory attachment as defined in claim 4 wherein the engagement force on a surface of the endoscope increases as a force is applied to move the accessory in a longitudinal direction relative to the endoscope in a proximal direction.

6. An endoscopic accessory attachment as defined in claim 1 further comprising a top surface and an inclined bottom surface on the wedge angled to correspond with the ramp surface of the accessory and oriented in the opposite direction from the ramp surface such that the bottom surface and ramp surface are in mating contact such that the top surface of the wedge is substantially parallel to the longitudinal axis of the bracing member.

7. An endoscopic accessory attachment as defined in claim 1 wherein the bracing member is configured to engage the surface of a working channel of the endoscope.

8. An endoscopic accessory attachment as defined in claim 1 wherein the bracing member comprises a surface configured to engage at least a portion of an outside surface of the distal end of the endoscope.

9. An endoscopic accessory attachment as defined in claim 8 wherein the bracing member surface is a cylindrical member that engages the entire circumference of the distal end of the endoscope.

10. An endoscopic accessory attachment as defined in claim 8 wherein the bracing member surface is inclined at an acute angle to the longitudinal axis of the endoscope.

11. An endoscopic accessory attachment as defined in claim 9 wherein the wedge comprises an annulus, separable from the accessory.

12. An endoscopic accessory attachment as defined in claim 1 further comprising a biasing member to bias the wedge toward the proximal end of the ramp.

13. An endoscopic accessory attachment as defined in claim 1 further comprising means positioned on the wedge for engaging with a separate leverage tool configured to permit the user to slide the wedge along the ramp surface.

14. An endoscopic accessory comprising:
   a self-locking attachment mechanism that is configured to increase engagement force on an endoscope as a longitudinal force is applied to move the accessory longitudinally and relative to the endoscope.

15. An endoscopic accessory as defined in claim 14 wherein the mechanism is configured to increase engagement force when a longitudinal force is applied to the accessory in a distal direction.

16. An endoscopic accessory as defined in claim 14 wherein the engagement force increases as the longitudinal force is applied to the accessory in a proximal direction.

17. A method of securing an endoscopic accessory to a distal end of an endoscope comprising:
   providing an endoscope;
   providing an accessory having at least a first surface and a second surface at an acute angle to the first surface;
   placing the accessory in engagement with an endoscope such that the first surface of the accessory engages the surface of an endoscope in the parallel relationship and the second surface of the accessory places an increasing engagement force on a surface of the endoscope as a force is applied to move the accessory longitudinally relative to the endoscope.

18. A method of securing an endoscopic accessory as defined in claim 17 further comprising:
   providing a wedge and sliding the wedge relative to the second surface of the accessory to engage and apply engagement force on a surface of an endoscope which opposes a resisting force applied by the first surface of the accessory.

19. An endoscopic accessory attachment mechanism comprising:
   a wedge engageable with an outside surface of an endoscope,
   a cone, sized to fit closely over the surface of the wedge when it is engaged with the endoscope.

20. An endoscopic accessory attachment coupling comprising:
   proximal and distal ends,
   means for attaching to a distal end of an endoscope at the proximal end, and
   means for attaching to an endoscopic accessory at the distal end.

* * * * *